(12) United States Patent
Dai et al.

(10) Patent No.: US 12,390,550 B2
(45) Date of Patent: Aug. 19, 2025

(54) ANTI-MICROBIAL ARTICLES

(71) Applicant: Solventum Intellectual Properties Company, Maplewood, MN (US)

(72) Inventors: Minghua Dai, Plymouth, MN (US); Jie J. Liu, Woodbury, MN (US); Joseph C. Spagnola, Woodbury, MN (US); Stephen A. O. Olson, Maplewood, MN (US); Ta-Hua Yu, Woodbury, MN (US); Junkang J. Liu, Woodbury, MN (US); Lei Zhang, Shanghai (CN)

(73) Assignee: Solventum Intellectual Properties Company, Maplewood, MN (US)

( * ) Notice: Subject to any disclaimer, the term of this patent is extended or adjusted under 35 U.S.C. 154(b) by 568 days.

(21) Appl. No.: 17/782,439

(22) PCT Filed: Dec. 4, 2020

(86) PCT No.: PCT/IB2020/061536
§ 371 (c)(1),
(2) Date: Jun. 3, 2022

(87) PCT Pub. No.: WO2021/116861
PCT Pub. Date: Jun. 17, 2021

(65) Prior Publication Data
US 2023/0166000 A1 Jun. 1, 2023

Related U.S. Application Data

(60) Provisional application No. 62/945,435, filed on Dec. 9, 2019.

(51) Int. Cl.
*A61L 15/44* (2006.01)
*A61L 15/28* (2006.01)

(52) U.S. Cl.
CPC ............... *A61L 15/44* (2013.01); *A61L 15/28* (2013.01); *A61L 2300/104* (2013.01); *A61L 2300/406* (2013.01)

(58) Field of Classification Search
CPC .... A61L 15/44; A61L 2300/404; A61L 15/18; A61L 2300/60; A01N 25/34
See application file for complete search history.

(56) References Cited

U.S. PATENT DOCUMENTS 4,364,995 A   12/1982   Crawford et al.
4,472,480 A    9/1984   Olson
(Continued)

FOREIGN PATENT DOCUMENTS

CN        1295041 A    5/2001
CN      101489777 A    7/2009
(Continued)

OTHER PUBLICATIONS

Dai, "The creation of a novel fluorescent protein by guided consensus engineering", Protein Engineering, Design & Selection, 2007, vol. 20, No. 02, pp. 69-79.
(Continued)

*Primary Examiner* — Carlos A Azpuru

(57) ABSTRACT

An article. The article includes a substrate, wherein the substrate having two opposing major surfaces; and particles coated with a metal oxide on the substrate: particles coated with a metal on the substrate; wherein the coated particles are randomly distributed on or in the substrate; and wherein at least some of coated particles are discrete particles.

17 Claims, 1 Drawing Sheet

(56) References Cited

U.S. PATENT DOCUMENTS

| | | | |
|---|---|---|---|
| 5,622,711 | A | 4/1997 | Chen |
| 5,633,010 | A | 5/1997 | Chen |
| 5,681,575 | A | 10/1997 | Burrell et al. |
| 5,753,251 | A | 5/1998 | Burrell et al. |
| 6,303,183 | B1 | 10/2001 | Wilczynski et al. |
| 7,745,509 | B2 | 6/2010 | Burton et al. |
| 8,664,149 | B2 | 3/2014 | Brady et al. |
| 10,881,882 | B1 | 1/2021 | Schwarz et al. |
| 2006/0188580 | A1 | 8/2006 | Sacks |
| 2013/0295150 | A1 | 11/2013 | Chantalat et al. |
| 2016/0220728 | A1* | 8/2016 | Adams ................ A61K 8/20 |
| 2019/0091466 | A1 | 3/2019 | Del Rossi et al. |

FOREIGN PATENT DOCUMENTS

| | | | |
|---|---|---|---|
| CN | 102448504 | A | 5/2012 |
| CN | 104304318 | A | 1/2015 |
| CN | 110139680 | A | 8/2019 |
| EP | 0427858 | A1 | 5/1991 |
| WO | 9009736 | A1 | 9/1990 |
| WO | 02087339 | A1 | 11/2002 |
| WO | 2005079913 | A1 | 9/2005 |
| WO | 2017004231 | A1 | 1/2017 |
| WO | 2017004582 | A1 | 1/2017 |
| WO | WO-2018075259 A1 * | | 4/2018 ............. A61L 15/18 |

OTHER PUBLICATIONS

International Search Report for PCT International Application No. PCT/IB2020/061536, mailed on Mar. 1, 2021, 5 pages.

* cited by examiner

ANTI-MICROBIAL ARTICLES

CROSS REFERENCE TO RELATED APPLICATIONS

This application is a national stage filing under 35 U.S.C. 371 of PCT/IB2020/061536, filed Dec. 4, 2020, which claims the benefit of Provisional Application No. 62/945,435, filed Dec. 9, 2019, the disclosure of which is incorporated by reference in its/their entirety herein.

BACKGROUND

The risk of being infected from medical devices is particularly high in the medical field. Anti-microbial articles or coatings are used extensively to prevent/reduce infections in the medical community. For example, medical devices used by doctors, including orthopedic pins, plates and implants, wound dressings, etc., must constantly guard against infection. Metallic ions with anti-microbial properties, such as Ag, Au, Pt, Pd, Ir, Cu, Sn, Sb, Bi and Zn, were used as anti-microbial compounds. Of these metallic ions, silver is well known due to its highly effective bioactivity, and various silver salts, complexes and colloids have been greatly utilized in medical devices to prevent and control infection.

SUMMARY

Although soluble salts of silver have been currently used to prevent microbial infections, they do not provide prolonged release of silver ions due to loss through removal or complexation of the free silver ions. They must be reapplied periodically to address this problem. Reapplication is often burdensome or even impractical, for example, when implanted medical devices are involved. Thus, it is desirable to have an anti-microbial article to provide a more effective and sustained release of anti-microbial agents.

In various exemplary embodiments described herein, the disclosed articles may be used to prevent microbial infections. The disclosed articles may be useful to provide an enhanced release of anti-microbial agents and thus to provide an enhanced anti-microbial activity.

In one aspect, the disclosure provides an article, the article comprising, a substrate, wherein the substrate having two opposing major surfaces: and particles coated with a metal oxide on the substrate; particles coated with a metal on the substrate; wherein the coated particles are randomly distributed on or in the substrate; and wherein at least some of coated particles are discrete particles Other features and aspects of the present disclosure will become apparent by consideration of the detailed description.

BRIEF DESCRIPTION OF THE DRAWINGS

The disclosure may be more completely understood in consideration of the following detailed description of various embodiments of the disclosure in connection with the accompanying drawings, in which it is to be understood by one of ordinary skill in the art that the drawings illustrate certain exemplary embodiments only, and are not intended as limiting the broader aspects of the present disclosure.

DETAILED DESCRIPTION

In the following description, reference is made to the accompanying set of drawings that form a part of the description hereof and in which are shown by way of illustration several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. At the very least, and not as an attempt to limit the application of the doctrine of equivalents to the scope of the claimed embodiments, each numerical parameter should at least be construed in light of the number of reported significant digits and by applying ordinary rounding techniques. In addition, the use of numerical ranges with endpoints includes all numbers within that range (e.g. 1 to 5 includes 1, 1.5, 2, 2.75, 3, 3.80, 4, and 5) and any narrower range or single value within that range.

Various exemplary embodiments of the disclosure will now be described with particular reference to the Drawings. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Figure 1:
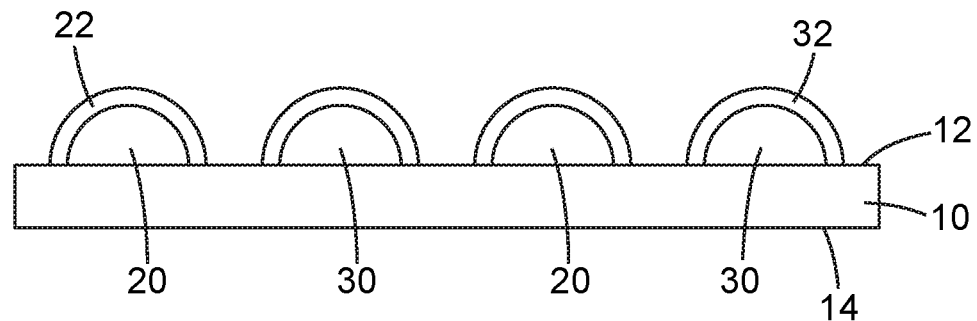
FIG. 1 is a cross-sectional view of an embodiment of an anti-microbial article of the present disclosure.

An article is disclosed herein. FIG. 1 is a cross-sectional view of an embodiment of article 1. Overall, article 1 includes a substrate 10 having two opposing major surfaces 12 and 14, article 1 includes particles 20 coated with a metal oxide 22 on the substrate 10, article 1 includes particles 30 coated with a metal 32 on the substrate 10. In the embodiment shown in FIG. 1, particles 20 and particles 30 are on the same opposing major surfaces. Alternatively, particles 20 and particles 30 may be on the different opposing major surfaces, for example, particles 20 coated with a metal oxide on the major surface 12 and particles 30 coated with a metal on the major surface 14. The coated particles 20 and 30 may be randomly distributed on or in the substrate. In some embodiments, at least some of coated particles 20 and 30 are discrete particles. In some embodiments, all of coated particles 20 and 30 are discrete particles. In some embodiments, the article may further comprise a release liner overlaying the coated particles.

In some embodiments, the surface of the substrate is partially covered with particles so that the substrate surface is partially exposed. In some embodiments, 2% to 95% of the substrate surface area is not covered by particles. In some embodiments, 20% to 80% of the substrate surface area is not covered by particles. In some embodiments, 2% to 50% of the substrate surface area is not covered by particles. In some embodiments, 2% to 30% of the substrate surface area is not covered by particles.

In some embodiments, at least 5% of the substrate surface area is covered with particles. In some embodiments, at least 10% of the substrate surface area is covered with particles. In some embodiments, at least 20% of the substrate surface area is covered with particles. In some embodiments, at least 40% of the substrate surface area is covered with particles. In some embodiments, at least 50% of the substrate surface area is covered with particles. In some embodiments, at least 70% of the substrate surface area is covered with particles. In some embodiments, at least 85% of the substrate surface area is covered with particles.

In some embodiments, no more than 98% of the substrate surface area is covered with particles. In some embodiments, no more than 95% of the substrate surface area is covered with particles. In some embodiments, no more than 90% of the substrate surface area is covered with particles. In some embodiments, no more than 85% of the substrate surface area is covered with particles. In some embodiments, no more than 70% of the substrate surface area is covered with particles. In some embodiments, no more than 50% of the substrate surface area is covered with particles. In some embodiments, no more than 40% of the substrate surface area is covered with particles. In some embodiments, no more than 30% of the substrate surface area is covered with particles.

The article of the present disclosure can be used to provide an anti-microbial effect. The article can be provided to a health care provider and can be applied to a subject to release anti-microbial agents. The article of the present disclosure provides synergistic antimicrobial functionality, a faster contact kill performance with lower silver oxide coating, for example, less than 20 mg silver oxide per 100 cm$^2$, preferably less than 10 mg silver oxide per 100 cm$^2$ or even more preferably less than 5 mg silver oxide per 100 cm$^2$.

In some embodiments, the article contains less than 20 micrograms/cm$^2$, less than 10 micrograms/cm$^2$, or less than 5 micrograms/cm$^2$ of silver oxide. In some embodiments, the article contains greater than 2 micrograms/cm$^2$ of silver oxide. In one embodiment, the article contains about 2.5 to 15 micrograms/cm$^2$ of silver oxide.

In some embodiments, the article contains less than 10 micrograms/cm$^2$, less than 5 micrograms/cm$^2$, less than 2 micrograms/cm$^2$, or less than 1 microgram/cm$^2$ of copper. In some embodiments, the article contains greater than 0.1 micrograms/cm$^2$ of copper. In one embodiment, the article contains about 0.15 to 3 micrograms/cm$^2$ of copper.

In some embodiments the article contains about 2.5-15 micrograms/cm$^2$ of silver oxide and about 0.2-3 micrograms/cm$^2$ of copper.

In some embodiments, the coated particles can be randomly distributed on or in one or more sections of the substrate. A section of the substrate can be defined as a portion of one major surface that is smaller in surface area than the overall surface area of the one major surface. The overall surface area of the one major surface can be defined by the outer edges of the substrate. The surface area of a section can be defined as the surface area of the substrate containing distributed particles. In some embodiments, the coated particles are randomly distributed on or in a section of the substrate. In some embodiments, the coated particles are randomly distributed on or in a section of the substrate and the section of substrate contains less than 20 micrograms/cm$^2$, less than 10 micrograms/cm$^2$, or less than 5 micrograms/cm$^2$ of silver oxide. In some embodiments, the coated particles are randomly distributed on or in a section of the substrate and the section of substrate contains greater than 2 micrograms/cm$^2$ of silver oxide. In one embodiment, the section of the substrate contains about 2.5 to 15 micrograms/cm$^2$ of silver oxide. In one embodiment, the section of the substrate is a hydrocolloid polymer that contains about 2.5 to 15 micrograms/cm$^2$ of silver oxide.

In some embodiments, the coated particles are randomly distributed on or in a section of the substrate and the section of substrate contains less than 10 micrograms/cm$^2$, less than 5 micrograms/cm$^2$, less than 2 micrograms/cm$^2$, or less than 1 microgram/cm$^2$ of copper. In some embodiments, the coated particles are randomly distributed on or in a section of the substrate and the section of substrate contains greater than 0.1 micrograms/cm$^2$ of copper. In one embodiment, the section of substrate contains about 0.15 to 3 micrograms/cm$^2$ of copper.

In some embodiments, the coated particles are randomly distributed on or in a section of the substrate and the section of substrate contains about 2.5-10 micrograms/cm$^2$ of silver oxide and about 0.2-3 micrograms/cm$^2$ of copper.

In some embodiments, the particles are randomly distributed on or in one or more islands on the substrate. An island includes a section of substrate containing particles that is completely surrounded by a section of substrate that does not contain particles. An island also includes a section of substrate containing particles that is partially surrounded by a section of substrate that does not contain particles and an edge of the substrate or an edge of the article. In some embodiments, the island contains about 2.5-10 micrograms/cm$^2$ of silver oxide. In some embodiments, the island contains about 0.15 to 3 micrograms/cm$^2$ of copper. In some embodiments, the island contains about 2.5-10 micrograms/cm$^2$ of silver oxide and 0.2-3 micrograms/cm$^2$ of copper.

In some embodiments, at least one major surface of the substrate contains about 2.5 to 15 micrograms/cm$^2$ of silver oxide. In some embodiments, at least one surface of the substrate contains about 0.15 to 3 micrograms/cm$^2$ of copper. In some embodiments, at least one surface of the substrate contains about 2.5-15 micrograms/cm$^2$ of silver oxide and about 0.2-3 micrograms/cm$^2$ of copper.

The particles are commonly distributed on the surface of the substrate.

In some embodiments, the coated particles are distributed on one major surface of the substrate and the concentration of silver oxide on the one major surface is about 2.5 to 15 micrograms/cm$^2$. In some embodiments, the coated particles are distributed on one major surface of the substrate and the concentration of copper on the one major surface is about 0.15 to 3 micrograms/cm$^2$. In some embodiments, the coated particles are distributed on one major surface of the substrate with the concentration of silver oxide on the major surface being about 2.5 to 15 micrograms/cm$^2$ and the concentration of copper on the major surface being about 0.15 to 3 micrograms/cm$^2$. In some embodiments, the coated particles are distributed on one major surface of the substrate with the concentration of silver oxide on the major surface being about 2.5 to 15 micrograms/cm$^2$, the concentration of copper on the major surface being about 0.15 to 3 micrograms/cm$^2$ and the substrate being a hydrocolloid polymer.

In some embodiments, the coated particles are distributed on at least one major surface of the substrate and the concentration of silver oxide on the at least one major surface major surface is about 2.5 to 15 micrograms/cm$^2$. In some embodiments, the coated particles are distributed on at least one major surface of the substrate and the concentration of copper on the at least one major surface is about 0.15 to 3 micrograms/cm$^2$.

Substrate

The substrate can be selected from foam, mesh, netting, woven, nonwoven, cotton, cellulose fabrics, perforated film, hydrocolloid, hydrogel, polymers with inherent porosity, pressure sensitive adhesive and combination of thereof. In some embodiments, the substrate can be an absorbent substrate selected from foam, mesh, netting, woven, nonwoven, cotton, cellulose fabrics, perforated film, hydrocolloid, hydrogel, polymers with inherent porosity, pressure sensitive adhesive and combination of thereof. Exemplary absorbent substrate can include film, fabrics or porous article made from viscose, rayon, alginate, gauze, biopolymers, polyurethane, biodegradable polymers or the polymers described in U.S. Pat. No. 7,745,509, the disclosures of which is hereby incorporated by reference. The absorbent materials used in the absorbent substrate can be manufactured of any suitable materials including, but not limited to, woven or nonwoven cotton or rayon or netting and perforated film made from nylon, polyester or polyolefins. Absorbent pad can be used as the absorbent layer and can be useful for containing a number of substances, optionally including drugs for transdermal drug delivery, chemical indicators to monitor hormones or other substances in a patient, etc.

The absorbent layer may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof. Absorbent layer can be manufactured of other synthetic and natural hydrophilic materials including polymer gels and foams.

In one embodiment the substrate is a hydrocolloid polymer.

Particles

The particles of the present disclosure can be any suitable particles, for example, non-metal particles. In some embodiments, the particle material can be an electrical insulator, for example, cellulose particles. The cellulose in the particles, can be powdered cellulose or can be modified celluloses, such as methylcellulose, cellulose acetate, and, and hydroxypropylmethylcellulose. The particles can be any suitable plastic particles. For example, polystyrene particles, polyethylene particles, polypropylene particles, PET particles, poly(methylmethacrylate) particles, and polyurethane particles can be used. Plastic particles can be made of natural and/or synthetic polymers. Plastic particles can be made of a single polymer or a blend of polymers.

The size of particles can be from about 1 micrometer to about 1000 micrometers, from about 1 micrometer to about 500 micrometers or from about 1 micrometer to about 100 micrometers.

The metal oxide to coat the particles of the present disclosure can be those known to have an anti-microbial effect. For most medical use, the metal oxide can also be biocompatible. In some embodiments, the metal oxide can include, but not limited to, silver oxide, copper oxide, gold oxide, zinc oxide, magnesium oxide, titanium oxide, chromium oxide and combinations thereof. In some of these embodiments, the metal oxide can be silver oxide, including but not limited to, $Ag_xO_y$, either x=2 and y=1 or x=y=4. In some embodiments, the metal oxide is $Ag_2O$.

The particles can be coated by metal oxide through any suitable means, for example, by physical vapor deposition techniques. The physical vapor deposition techniques can include, but is not limited to, vacuum or arc evaporation, sputtering, magnetron sputtering and ion plating. Suitable physical vapor deposition techniques can include those described in U.S. Pat. Nos. 4,364,995; 5,681,575 and 5,753,251, the disclosures of which are hereby incorporated by reference.

For, metal oxide coating, by the controlled introduction of reactive material, for example, oxygen into the metal vapor stream of vapor deposition apparatus during the vapor deposition of metals onto particles, controlled conversion of the metal to metal oxides can be achieved. Therefore, by controlling the amount of the reactive vapor or gas introduced, the proportion of metal to metal oxide in the metal oxide layer can be controlled. For 100% conversion of the metal to metal oxides at a given level of the layer, at least a stoichiometric amount of the oxygen containing gas or vapor is introduced to a portion of the metal vapor stream. When the amount of the oxygen containing gas increases, the metal oxide layer will contain a higher weight percent of metal oxide. The ability to achieve release of metal atoms, ions, molecules or clusters on a sustainable basis can be affected by varying the amount of the oxygen containing gas. As the amount of metal oxide increases when the level of oxygen containing gas introduced increases, metal ions released from the article in turn increases. Thus, a higher weight percent of metal oxide can, for example, provide an enhanced release of anti-microbial agents, such as metal ions and provide an increased anti-microbial activity.

The metal oxide can be formed as a thin film. The film can have a thickness no greater than that needed to provide release of metal ions on a sustainable basis over a suitable period of time. In that respect, the thickness will vary with the particular metal in the coating (which varies the solubility and abrasion resistance), and with the amount of the oxygen containing gas or vapor introduced to the metal vapor stream. The thickness will be thin enough that the metal oxide layer does not interfere with the dimensional tolerances or flexibility of the article for its intended utility. Typically, the metal oxide layer has a thickness of less than 1 micron. However, it is understood that increased thicknesses may be used depending on the degree of metal ion release needed over a period of time.

The metal to coat the particles of the present disclosure can be those known to have a positive electric potential. In some embodiments, the metal can include, but is not limited to, zinc, magnesium, aluminum, iron, calcium, tin, copper, titanium, chromium, nickel and alloys thereof.

The particles can be coated by metal through any suitable means, for example, by vapor deposition techniques. The vapor deposition techniques can include, but is not limited to, vacuum or arc evaporation, sputtering, magnetron sputtering and ion plating. Suitable physical vapor deposition techniques can include those described in U.S. Pat. Nos. 4,364,995; 5,681,575 and 5,753,251, the disclosures of which are hereby incorporated by reference.

The metal can be formed as a thin film. The film can have a thickness no greater than that needed to provide release of metal ions on a sustainable basis over a suitable period of time. In that respect, the thickness will vary with the particular metal in the coating (which varies the solubility and abrasion resistance), and with the amount of the oxygen containing gas or vapor introduced to the metal vapor stream. The thickness will be thin enough that the metal layer does not interfere with the dimensional tolerances or flexibility of the article for its intended utility. Typically, the metal layer has a thickness of less than 1 micron. However, it is understood that increased thicknesses may be used depending on the degree of metal ion release needed over a period of time.

In some embodiments, the ratio of metal oxide to metal of the article is from 10:1 to 1:10, from 9:1 to 1:9, from 8:1 to 1:8, from 7:1 to 1:7, from 6:1 to 1:6, from 5:1 to 1:5, from 4:1 to 1:4, from 3:1 to 1:3, or from 2:1 to 1:2. In some embodiments, the ratio of metal oxide to metal of the article is 5:1.

Figure 2:
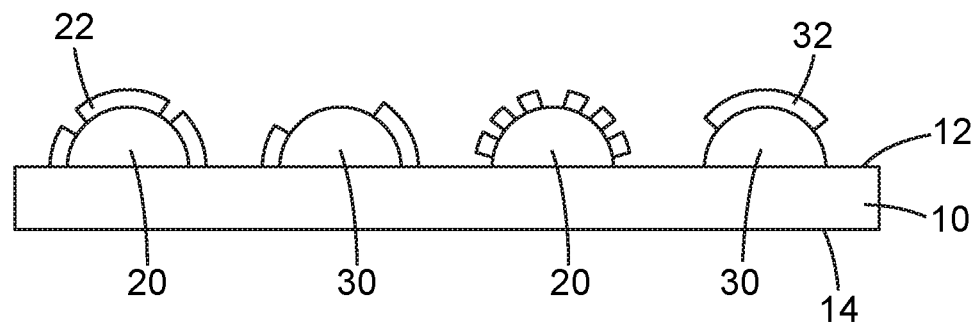
FIG. 2 is a cross-sectional view of an embodiment of an anti-microbial article of the present disclosure.

The metal oxide and/or metal coated particles can be fully coated or partially coated. In the embodiment shown in FIG. 1, particles 20 are fully coated with the metal oxide 22 and particles 30 are fully coated with the metal 32. In some embodiments shown in FIG. 2, the surface of the particles 20 or particles 30 is partially covered with the metal oxide 22 or the metal 32 so that the particle surface is partially exposed. Partially coated particles contain both coated and uncoated areas on the particle surface. In some embodiments, at least some of the metal oxide coated particles are partially coated. In some embodiments, at least some of the metal coated particles are partially coated.

For partially coated particles, at least some of the particle surface is exposed. In some embodiments, at least 5%, 10%, 20%, 30%, 50%, or 70% of the particle surface is exposed (i.e. uncoated). In some embodiments, no more than 95%, 90%, 80%, 70%, 60%, 50%, 40%, 30%, 20%, or 10% of the particle surface is exposed (i.e. uncoated).

In some embodiments, the article contains partially coated particles having at least 10% of the particle surface exposed (i.e. uncoated). In some embodiments, the article contains partially coated particles having at least 20% of the particle surface exposed (i.e. uncoated). In some embodiments, the article contains partially coated particles having at least 30% of the particle surface exposed (i.e. uncoated). In some embodiments, the article contains partially coated particles having at least 50% of the particle surface exposed (i.e. uncoated).

In some embodiments, the exposed particle surface is cellulose or modified cellulose. In some embodiments, the exposed particle surface is a polymer that is an electrical insulator.

In some embodiments, the article contains partially coated particles having at least 10% of the particle surface coated. In some embodiments, the article contains partially coated particles having at least 20% of the particle surface coated. In some embodiments, the article contains partially coated particles having at least 30% of the particle surface coated. In some embodiments, the article contains partially coated particles having at least 50% of the particle surface coated. In some embodiments, the article contains partially coated particles having at least 75% of the particle surface coated. In some embodiments, the article contains partially coated particles having at least 85% of the particle surface coated.

In some embodiments, the article contains partially coated particles having no more than 95%, 90%, 85%, or 75% of the particle surface coated. In some embodiments, the article contains partially coated particles having no more than 90/a of the particle surface coated.

In some embodiments, the partially coated particles are metal oxide coated particles. In some embodiments, the partially coated particles are silver oxide coated particles. In some embodiments, the partially coated particles are metal coated particles. In some embodiments, the partially coated particles are copper coated particles.

Optional Components

Suitable release liners can be made of Kraft papers, polyethylene, polypropylene, polyester or composites of any of these materials. In one embodiment, the package that contains the adhesive dressing may serve as a release liner. In one embodiment, the liners are coated with release agents such as fluorochemicals or silicones. For example, U.S. Pat. No. 4,472,480, the disclosure of which is hereby incorporated by reference, describes low surface energy perfluorochemical liners. In one embodiment, the liners are papers, polyolefin films, or polyester films coated with silicone release materials.

Properties

The article can generate at least one electrical current when introduced to an electrolytic solution. In some embodiments, the article is capable of generating a current in a range from about 10 µA to about 5000 µA when introduced to an electrolytic solution. In some embodiments, the article is capable of generating a current in a range from about 100 µA to about 1000 µA when introduced to an electrolytic solution. In the presence of an electrically conducting solution, redox reactions may take place, and thus currents may be produced between the metal oxide layer and the metal layer. For example, when the metal oxide layer includes silver oxide and the metal layer includes zinc, silver oxide is the cathode (positive electrode) and zinc is the anode (negative electrode), because the electrons follow from zinc to silver oxide. The flow of ions generates the electrical current. Thus, when the article of the present application is used as a wound dressing, it can recreate a physiologic current, which is important to the induction of neutrophil, macrophage and fibroblast cells essential to the healing process. In addition, the current can stimulates regional nerve endings to promote their involvement in wound resolution. Further, the current can inhibit the growth of bacteria. Therefore, the current generated by the article can have synergistic antimicrobial functionality along with $Ag^+$ release from the article.

The article can generate a more than 6.2, more than 6.5, more than 7, more than 8, more than 9 pH of when in contact with water. Not bound by the theory, the higher pH level generated when the article is in contact with water, may enhance the antimicrobial functionality of the article.

Various exemplary embodiments of the present disclosure are further illustrated by the following listing of embodiments, which should not be construed to unduly limit the present disclosure:

EMBODIMENTS

Embodiment 1 is an article, the article comprising, a substrate, wherein the substrate having two opposing major surfaces; and particles coated with a metal oxide on the substrate; particles coated with a metal on the substrate; wherein the coated particles are randomly distributed on or in the substrate; and wherein at least some of coated particles are discrete particles.

Embodiment 2 is the article of embodiment 1, wherein the metal oxide is selected from silver oxide, copper oxide, platinum oxide, zinc oxide, magnesium oxide, titanium oxide, chromium oxide and combinations thereof.

Embodiment 3 is the article of any of embodiments 1 to 2, wherein the metal oxide is silver oxide.

Embodiment 4 is the article of any of embodiment 3, wherein the silver oxide is $Ag_xOy$, either x=2 and y=1 or x=y=4.

Embodiment 5 is the article of any of embodiments 1 to 4, wherein the metal is selected from zinc, magnesium, aluminum, iron, calcium, tin, copper, titanium, chromium, nickel and alloys thereof.

Embodiment 6 is the article of any of embodiments 1 to 5, wherein the ratio of metal oxide to metal is from 10:1 to 1:10.

Embodiment 7 is the article of any of embodiments 1 to 6, wherein the ratio of metal oxide to metal is 5:1.

Embodiment 8 is the article of any of embodiments 1 to 7, further comprising a release liner overlaying the coated particles.

Embodiment 9 is the article of any of embodiments 1 to 8, wherein the article is capable of generating a current in a range from about 1 µA to about 5000 µA when introduced to an electrolytic solution.

Embodiment 10 is the article of any of embodiments 1 to 9, wherein the article is capable of generating a current in a range from about 100 µA to about 1000 µA when introduced to an electrolytic solution.

Embodiment 11 is the article of any of embodiments 1 to 10, wherein the substrate is selected from foam, mesh, netting, woven, nonwoven, cotton, cellulose fabrics, perforated film, hydrocolloid, hydrogel, polymers with inherent porosity, pressure sensitive adhesive and combination of thereof.

Embodiment 12 is the article of any of embodiments 1 to 11, wherein the article is an antimicrobial article.

Embodiment 13 is the article of any of embodiments 1 to 12, wherein the article is an antimicrobial article for treating Acne.

Embodiment 14 is the article of any of embodiments 1 to 13, wherein all of coated particles are discrete particles.

Embodiment 15 is the article of any of embodiments 1 to 14, wherein the particles are non-metal particles.

Embodiment 16 is the article of any of embodiments 1 to 15, wherein the particles coated with the metal oxide are partially coated with the metal oxide.

Embodiment 17 is the article of any of embodiments 1 to 16, wherein the particles coated with the metal are partially coated with the metal.

Embodiment 18 is the article of any of embodiments 1 to 17, wherein the surface of the substrate is partially covered with particles.

Embodiment 19 is the article of any of embodiments 1 to 18, 2% to 95% of the substrate surface area is not covered by particles.

Embodiment 20 is the article of any of embodiments 1 to 19, 2% to 50% of the substrate surface area is not covered by particles.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Preparation of Copper Coated Particles by Physical Vapor Deposition (Hydroxypropyl)methyl cellulose particles (product number H7509, obtained from the Sigma-Aldrich Corporation, St. Louis, MO) were placed in an oven at 100° C. oven for greater than 24 hours to remove excess water. The dried particles (14.94 g) were loaded into a 40 mL paddle-drum particle agitator (apparatus design as described in FIGS. 2 and 3 in U.S. Pat. No. 8,664,149, the disclosure of which is hereby incorporated by reference). The agitator was located in a sputtering vacuum chamber and the chamber was pumped down to a base pressure of $5.6 \times 10^{-6}$ Torr. A 3 inch (7.62 cm) diameter×0.25 inch (0.63 cm) copper sputtering target (99.999% purity, Kurt J Lesker Company, Jefferson Hills, PA) was used as the copper material source and the process pressure was 10 mTorr. After reaching base pressure, 100 sccm (standard cubic centimeters per minute) argon gas was flowed to the vacuum chamber and directly to the particle agitator. The paddle-drum was rotated at 6 rpm (revolutions per minute) and copper was deposited on the substrate via a 0.1 kW DC sputtering process for 1 hour and 36 minutes (467 volts). Based on the amount of copper removed from the target and the process efficiency of the apparatus, a 0.6 weight percent coating of copper was deposited on the particles.

Preparation of Silver Oxide Coated Particles by Physical Vapor Deposition (Hydroxypropyl)methyl cellulose particles (product number H7509, obtained from the Sigma-Aldrich Corporation) were placed in an oven at 100° C. oven for greater than 24 hours to remove excess water. The dried particles (15.49 g) were loaded into a 40 mL paddle-drum particle agitator (apparatus design as described in FIGS. 2 and 3 in U.S. Pat. No. 8,664,149). The agitator was located in a sputtering vacuum chamber and the chamber was pumped down to a base pressure of $2.5 \times 10^{-6}$ Torr. A 3 inch (7.62 cm) diameter× 0.25 inch (0.63 cm) thick silver sputtering target (99.99% purity, Kurt J Lesker Company) was used as the silver material source and the process pressure was 10 mTorr. After reaching base pressure, 90 sccm argon/10 sccm oxygen gas was flowed to the vacuum chamber and directly to the particle agitator. The paddle-drum was rotated at 6 rpm and silver was deposited on the substrate via a 0.1 kW DC sputtering process for 6 hours and 36 minutes (501 volts). Based on the amount of silver removed from the target and the process efficiency of the apparatus, a 6.0 weight percent coating of silver oxide was deposited on the particles.

Example 1. Preparation of Articles

Articles were prepared using 3 cm by 3 cm sections cut from TEGADERM Hydrocolloid Dressings #90002 (3M Corporation, Maplewood, MN) as the base material for the substrate. Silver oxide coated particles and copper coated particles were mixed together to form a mixed distribution of particles. The release liner was removed from each section of dressing and a measured amount of the mixture of coated particles was evenly sprinkled over the surface of the release liner. The hydrocolloid sheet was then placed on the release liner so that the particles were sandwiched between the surface of the release liner and the hydrocolloid surface. The particles were adhered to the surface of the hydrocolloid substrate using pressure from a hand roller. The roller was rolled back and forth multiple times over the surface of the release liner. The release liner was then removed to provide the finished article. Articles containing different concentrations (micrograms/cm$^2$) of silver oxide and copper were prepared by adjusting the amounts and ratios of particles added to an article surface. Comparative Articles were prepared containing only silver oxide coated particles or only copper coated particles. Control Articles were also prepared that contained the hydrocolloid substrate without any silver oxide coated particles or copper coated particles. Articles A-B and Comparative Articles A-D are described in Table 1.

Example 2. Testing of Articles for Antimicrobial Activity

The test method ASTM E2180-18 ('Standard Test Method for Determining the Activity of Incorporated Antimicrobial Agent(s) in Polymeric or Hydrophobic Materials') was used to evaluate the antibacterial activity of the articles. *Propionibacterium acnes* (*P. acnes*) ATCC 6919 was obtained from ATCC (Manassas, VA). A single colony of *P. acnes* from a stock agar culture was inoculated into Oxoid anaerobe basal broth (Oxoid Limited, Basingstoke, UK) and incubated at 37° C. for 18 hours to provide a 1-10×10$^8$ cfu/mL culture of *P. acnes*.

An agar slurry was prepared by dissolving 0.85 g NaCl and 0.3 g of agar (Teknova Incorporated, Hollister, CA) in 100 mL of deionized water. The slurry was heated with stirring on a hot plate until the agar dissolved. The agar slurry was sterilized for 15 minutes in an autoclave (set at 121° C., 15 psi) and then equilibrated to 45° C. An aliquot (1 mL) of the *P. acnes* culture (1-10×10$^8$ cfu/mL) was centrifuged (300 rpm for 5 minutes) to form a pellet of cells. The pellet was added to the agar slurry and mixed to yield a *P. acnes* concentration of 1-10×10$^6$ cfu/mL in the molten agar slurry.

For each article type three replicates were prepared and tested (n=3). Each finished article (prepared according to Example 1) was placed in a sterile 15×100 mm petri dish with the particle coated surface exposed. The exposed surface of the article was wetted by gently wiping the surface with a sterile cotton swab that had been dipped into a sterile 0.85% saline solution. The molten, inoculated agar slurry (0.2 mL) was applied to the wetted surface of the article using a pipette. The slurry was slowly applied at a low angle of incidence relative to the article surface and then spread over the entire surface using a plastic spreader. The agar coated article was placed in an incubator at 25° C. for 3 hours. Each incubated article was aseptically transferred to a 50 mL specimen tube containing 10 mL of 1× phosphate buffered saline (PBS) (obtained from Teknova Incorporated and sterilized by 0.2 micrometer filtration). The specimen tube was placed in a Branson 8510 ultrasonic bath (Branson Company, Danbury, CT) and sonicated for one minute. The tube was subsequently vortexed for one minute using a VWR analog vortex mixer (VWR International, Radnor, PA) with the mixing speed set at 6 (speed settings of 1-10 available). The sample was serially diluted seven times with PBS (10-fold dilutions). An aliquot (3 microliters) from the final dilution was added to an Oxoid anaerobe basal agar plate (Oxoid Limited). The plate was incubated at 37° C. for 16 hours. The colonies from each plate were counted by visual examination. The cfu counts of the individual plates (n=3) were averaged and the average count value was used to calculate (based on serial dilutions) the number of colony forming units per milliliter (cfu/mL) that were recovered from the inoculated article. In Table 1, the calculated cfu/mL values are reported.

TABLE 1

| Article | Coating weight of Silver Oxide (μg/cm$^2$) | Coating weight of Copper (μg/cm$^2$) | CFU/mL Recovered from the Article | Standard Deviation | Fold reduction in CFU/mL versus Control Article |
|---|---|---|---|---|---|
| Control Article | 0 | 0 | 3.2 × 10$^6$ | 1.9 × 10$^5$ | |
| Article A | 3.33 | 0.33 | 4.4 × 10$^4$ | 1.9 × 10$^4$ | 73 |
| Article B | 6.67 | 0.67 | 4.4 × 10$^2$ | 76 | 7273 |
| Comparative Article A | 10.0 | 0 | 1.7 × 10$^6$ | 1.2 × 10$^6$ | 2 |
| Comparative Article B | 20.0 | 0 | 1.0 × 10$^6$ | 3.3 × 10$^5$ | 3 |
| Comparative Article C | 0 | 0.25 | 2.1 × 10$^5$ | 1.7 × 10$^5$ | 15 |
| Comparative Article D | 0 | 0.67 | 1.3 × 10$^5$ | 9.9 × 10$^4$ | 25 |

Example 3. Preparation and Testing of Articles

Articles C-G, having a constant coating weight of silver oxide (3.33 micrograms/cm$^2$) and varying coating weights of copper (0.07, 0.21, 0.33, 0.50, or 0.62 micrograms/cm$^2$), were prepared according to the method of Example 1. The articles were tested for antimicrobial activity by the method of Example 2. The results are presented in Table 2.

TABLE 2

| Article | Coating weight of Silver Oxide (µg/cm$^2$) | Coating weight of Copper (µg/cm$^2$) | CFU/mL Recovered from the Article | Standard Deviation | Fold reduction in CFU/mL Count versus Control Article |
|---|---|---|---|---|---|
| Control Article | 0 | 0 | $1.4 \times 10^5$ | $1.6 \times 10^4$ | |
| Article C | 3.33 | 0.07 | $1.4 \times 10^4$ | $5.5 \times 10^3$ | 10 |
| Article D | 3.33 | 0.21 | $1.5 \times 10^3$ | $1.9 \times 10^2$ | 93 |
| Article E | 3.33 | 0.33 | 670 | 142 | 209 |
| Article F | 3.33 | 0.50 | 200 | 104 | 700 |
| Article G | 3.33 | 0.62 | 260 | 177 | 538 |

Example 4. Preparation and Testing of Articles

Articles H-K, having varying coating weights of silver oxide and copper, were prepared according to the method of Example 1. The articles were tested for antimicrobial activity by the method of Example 2. The results are presented in Table 3.

TABLE 3

| Article | Coating weight of Silver Oxide (µg/cm$^2$) | Coating weight of Copper (µg/cm$^2$) | CFU/mL Recovered from the Article | Standard Deviation | Fold reduction in CFU/mL Count versus Control Article |
|---|---|---|---|---|---|
| Control Article | 0 | 0 | $1.0 \times 10^6$ | $5.8 \times 10^5$ | |
| Article H | 0.83 | 0.09 | $5.9 \times 10^5$ | $1.6 \times 10^5$ | 2 |
| Article I | 1.66 | 0.17 | $1.1 \times 10^5$ | $6.9 \times 10^4$ | 9 |
| Article J | 3.33 | 0.33 | $6.7 \times 10^3$ | 0 | 149 |
| Article K | 6.67 | 0.67 | 30 | 24 | 33,333 |

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An article, the article comprising:
a substrate, wherein the substrate has two opposing major surfaces;
particles coated with a metal oxide on the substrate; and
particles coated with a metal on the substrate;
wherein the particles coated with the metal oxide and the particles coated with the metal are randomly distributed on or in the substrate; and
wherein at least some of the particles coated with the metal oxide and the particles coated with the metal are discrete particles.

2. The article of claim 1, wherein the metal oxide is selected from silver oxide, copper oxide, platinum oxide, zinc oxide, magnesium oxide, titanium oxide, chromium oxide and combinations thereof.

3. The article of claim 1, wherein the metal oxide is silver oxide.

4. The article of claim 3, wherein the silver oxide is $Ag_xO_y$, either x=2 and y=1 or x=y=4.

5. The article of claim 1, wherein the metal is selected from the group consisting of zinc, magnesium, aluminum, iron, calcium, tin, copper, titanium, chromium, and nickel.

6. The article of claim 1, wherein the ratio of metal oxide to metal is from 10:1 to 1:10 on a µg/cm$^2$ basis.

7. The article of claim 1, wherein the ratio of metal oxide to metal is 5:1 on a µg/cm$^2$ basis.

8. The article of claim 1, further comprising a release liner overlaying the particles coated with the metal oxide and the particles coated with the metal.

9. The article of claim 1, wherein the article is capable of generating a current in a range from about 1 µA to about 5000 µA when introduced to an electrolytic solution.

10. The article of claim 1, wherein the article is capable of generating a current in a range from about 100 µA to about 1000 µA when introduced to an electrolytic solution.

11. The article of claim 1, wherein the substrate is selected from foam, mesh, netting, woven, nonwoven, cotton, cellulose fabrics, perforated film, hydrocolloid, hydrogel, polymers with porosity, pressure sensitive adhesive and combination of thereof.

12. The article of claim 1, wherein the article is an antimicrobial article.

13. The article of claim 1, wherein the article is an antimicrobial article for treating Acne.

14. The article of claim 1, wherein all of the particles coated with the metal oxide and the particles coated with the metal arc discrete particles.

15. The article of claim 1, wherein the particles coated with the metal oxide and the particles coated with the metal are non-metal particles.

16. The article of claim 1, wherein the particles coated with the metal oxide are partially coated with the metal oxide.

17. The article of claim 1, wherein the particles coated with the metal are partially coated with the metal.

* * * * *